United States Patent [19]

Duan et al.

[11] Patent Number: 5,637,639
[45] Date of Patent: Jun. 10, 1997

[54] REDUCED SOLVENT PROCESS FOR PREPARATION OF AQUEOUS POLYURETHANE DISPERSIONS WITH IMPROVED HEAT-AND WATER-RESISTANCE

[75] Inventors: Youlu Duan, Maplewood; Sonja Stammler, Marine on the St. Croix, both of Minn.

[73] Assignee: H.B. Fuller Licensing and Financing, Inc., St. Paul, Minn.

[21] Appl. No.: 528,936

[22] Filed: Sep. 15, 1995

Related U.S. Application Data

[63] Continuation-in-part of Ser. No. 304,653, Sep. 9, 1994.
[51] Int. Cl.$^6$ .................. C08L 75/06; C08G 18/46
[52] U.S. Cl. .................. 524/591; 524/500; 524/507; 524/726; 524/760; 524/770; 524/840; 525/123; 525/127; 525/440; 525/454; 525/455; 525/457; 525/528; 528/71; 528/905
[58] Field of Search .................. 524/500, 507, 524/591, 726, 760, 770, 840; 525/123, 127, 440, 454, 455, 457, 528; 528/71, 905

[56] References Cited

U.S. PATENT DOCUMENTS

| | | | |
|---|---|---|---|
| 4,801,644 | 1/1989 | Coogan | 524/839 |
| 4,870,129 | 9/1989 | Henning et al. | 524/839 |
| 5,344,873 | 9/1994 | Blum | 524/591 |
| 5,508,340 | 4/1996 | Hart | 524/591 |
| 5,541,251 | 7/1996 | Bontinck et al. | 524/507 |

*Primary Examiner*—Rabon Sergent
*Attorney, Agent, or Firm*—Vidas Arrett & Steinkraus, P.A.

[57] ABSTRACT

A process for preparing poly(urethane/urea) prepolymers and aqueous poly(urethane/urea) dispersions (PUDs) therefrom, the poly(urethane/urea) polymers having high heat resistance and good water resistance. The method employs a water soluble volatile organic solvent, such as acetone, at a level of 0.1–5%, based on final dispersion weight, a level which does not require removal for purposes of flash point considerations. The method includes the steps of reacting in the presence of a water soluble volatile organic solvent at a level corresponding to no more than 5% by weight of the final dispersion, a polyisocyanate component comprising a diisocyanate, with a polyol component to produce an isocyanate terminated polyurethane prepolymer the polyol component providing both carboxylate groups and sulfonate groups;

dispersing the isocyanate terminated prepolymer in aqueous media;

reacting said dispersed isocyanate terminated polyurethane prepolymer with at least one amine functional chain extender or chain terminator compound to thereby form said poly(urethane/urea) polymer;

neutralizing the carboxylate and sulfonate groups of said isocyanate terminated prepolymer with an alkali hydroxide or a tertiary amine prior to, or simultaneous with, said reaction of said prepolymer and said amine functional chain extender or terminator;

wherein the method is performed without a solvent distillation step.

28 Claims, No Drawings

REDUCED SOLVENT PROCESS FOR PREPARATION OF AQUEOUS POLYURETHANE DISPERSIONS WITH IMPROVED HEAT-AND WATER-RESISTANCE

CROSS-REFERENCE TO RELATED APPLICATION

This application is a continuation-in-part of copending application Ser. No. 08/304,653, filed Sep. 9, 1994, incorporated herein by reference.

BACKGROUND OF THE INVENTION

1. Field of the Invention

This invention relates to a method for preparing aqueous anionic polyurethane dispersion adhesive compositions which provide good heat and water resistance.

2. Description of the Prior Art

Aqueous dispersions of polyurethanes are well known. Dispersion may be accomplished by use of an external surface active agent or by providing the polyurethane polymer backbone with non-ionic ethylene oxide ether moieties or by providing the polyurethane polymer with neutralized cationic or anionic groups.

For anionic aqueous polyurethane dispersions, the ionic salt groups are salts of carboxylic acid or sulfonic acid groups. In the preparation of anionic polyurethane dispersions it is generally preferred to prepare a polyurethane prepolymer having a small residual free isocyanate content, disperse the prepolymer in aqueous media, and then add a plural functional relatively low molecular weight primary and/or secondary amine as a chain extender. This chain extension process is needed because a higher molecular weight poly(urethane/urea) having better heat resistance is obtained after extension. To aid in dispersion of the isocyanate functional polyurethane prepolymer and sometimes to control the polyurethane forming reaction, a volatile solvent such as acetone, methyl ethyl ketone, N-methyl pyrrollidone or the like are employed in the prepolymer forming reaction. If the solvent level is high after dispersion, it usually must be substantially removed by distillation, a complicated process step requiring expensive equipment. Furthermore, the solvent removal step results in poor volume/time yield in the manufacturing process and the handling of large volumes of solvent in the reaction medium and in the removal step increases the risk of explosion or fire during the manufacturing process.

Polyurethane prepolymers produced in the manner just described are reaction products of a plural isocyanate compound (polyisocyanate) and a polyol component which includes a polymeric polyol such as a polyether polyol or a polyester polyol and, typically, a monomeric or very short chain oligomeric polyol. The polyurethane so produced will have a —(—A—B—)— type block polymer structure where the A segment is relatively soft segment derived from the polymeric polyol and the B segment is a hard segment derived from the polyisocyanate component and any monomeric or short oligomeric polyol in the polyol component. For nearly all of the commercial anionic aqueous polyurethane dispersion products, the ionic groups are contained in the hard segment.

In considering how to manufacture polyurethane dispersion products it must also be kept in mind the desired use properties of the final polymer. In the case of dispersions used as adhesive products, heat and water resistance are important properties which are significantly affected by the ingredients of the polyol component employed. For instance, increasing the total amount of ionic groups in the hard segment of the polymer can result in reduction of the relative amount of soft segment and reduce water resistance and flexibility and elasticity of the final polymer. Adding components which include non-ionic ethylene oxide ether or other polyether moieties may improve dispersability but likewise at the sacrifice of heat and water resistance.

Henning, et al., U.S. Pat. No. 4,870,129, discloses use of the sodium salt of N-(2-aminoethyl)-2-aminoethane sulfonic acid (AAS salt) to prepare polyurethane dispersions. The aqueous polyurethane dispersions are reported to have exhibited good stability at low pH values (5–7), but only medium heat resistance. Commercial products based on this monomer, such as Bayer KA-8464 show poor water resistance. Furthermore the process employed in this reference employs a level of acetone solvent, before removal by distillation, which is 80 weight percent of the dispersion. Removal of this amount of solvent is a very complicated process on a commercial scale. The sulphonate groups are incorporated into the hard segment when this compound is employed.

Reiff, et al, U.S. Pat. No. 4,108,814, discloses aqueous sulfonated polyurethane dispersions based on sulfonated polyether diols and a water soluble sulfonated diamine in a solvent free process. However, this solvent-free process produces a polymer which will not have a high crystallization rate, high heat resistance or good water resistance.

U.S. Pat. No. 5,334,690, to Schafheutle, et al, discloses a preparation of a polyurethane dispersion which employs a polyester or polyether diol having anionic groups. The reference indicates that the polyurethane may be prepared in the presence of a solvent or in a solvent-free melt process. In examples this reference utilizes a carboxylated polyester polyol and acetone at a level of about 40% is employed. A melt process is also exemplified using a sulfonated polyester polyol. However the high temperature used in a melt process can introduce side reactions such as diisocyanate reaction with carboxylic acid and/or urethane groups and even trimerization of the isocyanate so that the final product may not have a good linear structure and therefore the polymer may have poor crystallization rate, poor green strength, and inadequate heat resistance. Therefore a melt process is a less preferred process for preparing aqueous polyurethane dispersions.

A solvent-free or low solvent process for preparation of aqueous polyurethane dispersions is disclosed in U.S. Pat. No. 4,829,122, to Pedain, et al, but this process utilizes a blocked amine chain extender.

Duan et al in copending application Ser. No. 08/343,676, filed Nov. 22, 1994 as a continuation-in-part of application Ser. No. 08/126,508, filed Sep. 24, 1993, now abandoned, disclose aqueous polyurethane dispersions based on use of both sulfonated polyester polyols and a hydroxy carboxylic acid, suitably an α,α-dimethylol alkanoic acid such as dimethylolpropionic acid, which gives a polyurethane polymer having anionic groups on both hard and soft segments of the polymer. Acetone and solvent-free processes are used to prepare the polyurethane prepolymers and, in the case of the acetone process, after dispersion and chain extension the acetone is distilled off. In the solvent-free process the polyesters used in these formulations include ethylene oxide ether moieties due to use of diethylene glycol in the polyester and have a melting point below 50° C. and preferably ones which are liquid at room temperature. The polyurethanes produced in accordance with the solvent-free process have poor heat and water resistance.

Duan et al in copending application Ser. No. 08/304,653, filed Sep. 9, 1994, disclose aqueous polyurethane dispersions based on use of both sulfonated polyester polyols using a water compatible solvent such as acetone, NMP or DPMA and sulfonated polyesters of higher molecular weight and a low molecular weight non-carboxylated diol which has high heat resistance and good water resistance. In the case where NMP or DPMA are used, a range of about 3–15% solvent based on final dispersion weight is disclosed. In the case where acetone is used, after dispersion and chain extension, the acetone is distilled off so that the final level of acetone may be as little as 1.0% acetone or even less.

Surprisingly it has now been discovered that similar polymers to those of copending application Ser. No. 08/304, 653, having high heat and water resistance, can be produced by a low acetone solvent process which allows for good control of the prepolymer forming reaction but which does not incorporate so much solvent that it must be removed from the final dispersion.

SUMMARY OF THE INVENTION

This invention relates to an improved process for preparing poly(urethane/urea) prepolymers and aqueous poly(urethane/urea) dispersions (PUDs) therefrom, the poly(urethane/urea) polymers having high heat resistance and good water resistance. The inventive method employs a water soluble volatile organic solvent, such as acetone, at a level of 0.1 to about 5%, preferably no more than 3% and most preferably 0.5–2%, based on final dispersion weight, levels which do not require removal for purposes of flash point considerations. Accordingly, the invention provides a method for forming a stable aqueous dispersion of an anionic poly(urethane/urea) polymer, the dispersion comprising from about 0.1 to about 5% by weight of the dispersion of volatile solvents, the poly(urethane/urea) polymer when dried characterized by high heat and water resistance, the method comprising reacting in the presence of a water soluble volatile organic solvent at a level corresponding to no more than 5% by weight of the final dispersion, a polyisocyanate component comprising a diisocyanate, with a polyol component to produce an isocyanate terminated polyurethane prepolymer the polyol component providing both carboxylate groups and sulfonate groups;

dispersing the isocyanate terminated prepolymer in aqueous media;

reacting said dispersed isocyanate terminated polyurethane prepolymer with at least one amine functional chain extender or chain terminator compound to thereby form said poly(urethane/urea) polymer;

neutralizing the carboxylate and sulfonate groups of said isocyanate terminated prepolymer with an alkali hydroxide or a tertiary amine prior to, or simultaneous with, said reaction of said prepolymer and said amine functional chain extender or terminator;

wherein said method is preformed without a solvent distillation step.

Suitably the polyol component includes at least one sulfonated polyester, the sulfonated polyester characterized by number average molecular weights in the range of about 500 to 10,000 and melting temperatures between about 10° C. and 100° C.; and at least one hydroxy carboxylic acid of the formula:

$$(HO)_xR(COOH)_y$$

wherein R represents a straight or branched, hydrocarbon radical containing 1 to 12 carbon atoms, and x and y represent values from 1 to 3, provided, however, that when the value of x is 1, an equivalent amount of trifunctional isocyanate is employed in the polyisocyanate component and when x is 3, an equivalent amount of monofunctional isocyanate is employed whereby the resulting polyurethane prepolymer remains substantially non-crosslinked. Optionally the polyol component additionally comprises a non-sulfonated polyester polyol and/or a non-carboxylated low molecular weight diol. Desireably said polyol component is free of compounds comprising ethyleneoxyethylene groups and preferably the polyol component is free of any polyether moieties.

DETAILED DESCRIPTION OF THE INVENTION

The sulfonated polyester polyol preferably used to form the isocyanate terminated polyurethane prepolymer is a polyester polyol which incorporates sulfonate groups via sulfonate functional dicarboxylic acid residues and/or sulfonate functional diol residues. The sulfonate functional groups may be in acid or salt form. Suitable salt forms are alkali metal salts, or tertiary amine salts. Typically such sulfonate functional dicarboxylic acid residues and/or sulfonate functional diol residues are a minor portion of the diol and/or diacid moieties of the polyester, preferably 1.0%–10.0% by weight of the polyester. The non-sulfonated diacids and diols used in forming the sulfonated polyesters may be aromatic or aliphatic. Examples of the non-sulfonated diacids include adipic, azelaic, succinic, suberic and phthalic acids. Examples of the non-sulfonated diols include ethylene glycol, butanediol, butenediol, propanediol, neopentylglycol, hexanediol, 1,4-cyclohexane dimethanol, 1,2-propylene glycol and 2-methyl-1,3-propanediol. Examples of the sulfonate diacids include sulfoisophthalic acid, 1,3-dihydroxybutane sulfonic acid and sulfosuccinic acid. Examples of the sulfonate diols include 1,4 dihydroxybutane sulfonic acid and succinaldehyde disodium bisulfite.

Preferred such sulfonated polyester polyols include polyester polyols based on 5-sulfoisophthalic acid monosodium salt, adipic acid and 1,6-hexanediol.

The sulfonated polyester polyols useful in the invention suitably have number average molecular weights in the range of about 500 to 10,000, preferably 1,000–4,000, and melting temperatures between about 10° C. and 100° C. Preferred sulfonated polyester polyols have melting points between 40° C. and 60° C. Especially preferred are sulfonated polyester polyols prepared by reacting sulfonate diacids or diols with non-sulfonated short chain diols and short chain diacids or derivatives of diacids.

The polyol component utilized to make the poly(urethane/urea) dispersions of the invention include, in addition to the sulfonated polyester polyol, a hydroxy carboxylic acid, and may optionally also include a non-acidic polyester polyol and a non-acidic low molecular weight diol. For purposes of the present invention the polyols used in making the poly(urethane/urea) polymers desireably are free of ethyleneoxyethylene groups as such moieties contribute to poor moisture and heat resistance in the final polymer. Most preferably the polyol component is free of compounds having any polyether moieties thereon.

The carboxylate groups of the hydroxy alkanoic acid will offer additional water dispersibility for the resulting polyurethanes, in addition to sulfonate groups of the sulfonated polyester polyols. The hydroxy alkanoic acid provides anionic groups in the hard segment of the polyurethane polymer whereas the sulfonated polyester polyol provides anionic groups in the soft segment of the polymer. Without being bound thereby, it is believed that by providing anionic groups in both the hard and soft segments of the polymer, the anionic groups are able to more efficiently effect dispersion of the prepolymer and thereby allow for dispersion of polymers which provide high heat and water resistance using only a low amount of solvent. The carboxylate groups in the resulting polyurethanes can also function as crosslinking points for reaction with polyfunctional aziridines. The hydroxy carboxylic acids used to form the isocyanate terminated polyurethane prepolymer are compounds of the formula:

wherein R represents a straight or branched, hydrocarbon radical containing 1 to 12 carbon atoms, and x and y represent values from 1 to 3, provided, however, that when the value of x is 1, an equivalent amount of trifunctional isocyanate is employed and conversely when x is 3, an equivalent amount of monofunctional isocyanate is employed so that the resulting polyurethane prepolymer remains substantially non-crosslinked. Preferably, x is 2, and, more preferably, the hydroxy carboxylic acids are α,α-dimethylol alkanoic acids represented by the formula:

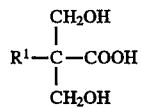

where $R^1$ denotes hydrogen or an alkyl group with up to about 9 carbon atoms. Examples of such compounds are 2,2-dimethylolacetic acid, 2,2-dimethylolpropionic acid, 2,2-dimethylolbutyric acid and 2,2-dimethylolpentanic acid. The preferred dihydroxyalkanoic acid is 2,2-dimethylolpropionic acid (DMPA).

The optional non-sulfonated polyester polyols employed in the polyol component used to prepare the isocyanate terminated prepolymer are generally less costly than the sulfonated polyester polyols. Non-sulfonated diacids and diols used in forming the non-sulfonated polyester polyols may be aromatic or aliphatic. Examples of the non-sulfonated diacids include adipic, azelaic, succinic, suberic and phthalic acids. Examples of the non-sulfonated diols include ethylene glycol, butanediol, butenediol, propanediol, neopentylglycol, hexanediol, 1,4-cyclohexane dimethanol, 1,2-propylene glycol and 2-methyl-1,3 propanediol.

In some embodiments, a low molecular weight diol may also be employed as part of the polyol component. The low molecular weight diols used in forming the isocyanate terminated polyurethane prepolymer are aliphatic diols, particularly alkylene diols. Their molecular weight range is from 60 to 400. Preferably, the low molecular weight diols are $C_2$-$C_8$ alkylene diols and most preferably $C_3$-$C_6$ alkylene diols examples of the low molecular weight diols are ethylene glycol, 1,3-propylene glycol, and more preferably, 1,4-butanediol (1,4-BD) and 1,6-hexanediol. Such low molecular weight diols can contribute to an increased crystallization rate, high green strength, water resistance and good heat resistance.

The diisocyanates which are used in forming the isocyanate terminated polyurethane prepolymer can be aliphatic or aromatic diisocyanates or their mixtures. Examples of suitable aliphatic diisocyanates are isophorone diisocyanate (IPDI), cyclopentylenediisocyanate, cyclohexylenediisocyanate, methylcyclohexylenediisocyanate, dicyclohexylmethanediisocyanate, hexamethylenediisocyanate (HDI), dicyclohexylmethanediisocyanate (H12MDI), and tetramethylxylenediisocyanate (TMXDI). Examples of suitable aromatic diisocyanates are phenylenediisocyanate, tolylenediisocyanate (TDI), xylylenediisocyanate, biphenylenediisocyanate, naphthylenediisocyanate and diphenylmethanediisocyanate (MDI).

The polyurethane prepolymer is formed in the presence of a small amount of volatile water soluble organic solvent having a boiling point below 100° C., of which acetone is preferred. The amount is such that upon dispersion and chain extension of the prepolymer the final dispersion will contain no more than about 5%, and preferably 0.5–3% solvent, without the need for a solvent removal step. Examples of other solvents which may be employed include 1-methyl-2-pyrrolidone (NMP), dipropylene glycol methyl ether acetate (DPMA), and methyl ethyl ketone (MEK).

In forming the dispersion water is suitably added to the prepolymer in an amount to provide a solids content in the completed dispersion of between about 20 and 50% by weight, desirably from about 30 to about 40% by weight.

The flash point of polyurethane dispersions containing various levels of acetone is shown in Table 1, below.

TABLE 1

| Acetone content | Flash point* (°F.) | |
|---|---|---|
| (weight %) | ASTM D-56 | ASTM D-3278 |
| 7 | 62 | 77 |
| 5 | 75 | 90 |
| 3 | 102 | 130 |
| 2 | >140 | >140 |
| 1 | >150** | >150** |

*Flash point of pure acetone is 15° F.
**The water vapor in the aqueous polyurethane dispersion having 1% acetone by weight interferes with the flash point at the temperate higher than 150° F., so 150° F. represents the maximum flash point measurable by the test method.

From the foregoing it can be seen that an acetone level of no more than 5%, preferably no more than about 3%, and most preferably no more than 2%, provides a desirable formulation in that it has little or no potential for solvent flashing.

In the polyol component the polyols are suitably employed in the following relative weight ratios of sulfonated polyester polyol/hydroxy carboxylic acid/non-acidic low molecular weight diol/non-sulfonated polyol: 10–50/0.5–5/0.1–2/0–20, preferably: 20–40/1–3/0.5–1.5/0–10. In forming the polyurethane prepolymer the ratio of NCO groups in the diisocyanate component to OH groups in the polyol component is suitably 1.1–1.9, preferably 1.2–1.6.

The prepolymer suitably is reacted to provide a NCO level of 1–5% by weight.

The polyurethane prepolymer is formed at a temperature from room temperature to 100° C., typically at a temperature of 50°–80° C. A catalyst, such as a tertiary amine or tin salt catalyst may be employed if desired.

After the prepolymer is formed, it is dispersed in water. To accomplish dispersion, the sulfonate groups, if not already in salt form, and at least a portion of the carboxylic acid groups of the prepolymer are neutralized with a tertiary amine. The tertiary amine may be added with the water, but more preferably neutralization is accomplished before the water is added, suitably by direct addition to the prepolymer/solvent mixture.

After addition of the tertiary amine, the acid number of the dispersion should be no more than 15, preferably less than 5 and more preferably the tertiary amine is in excess of the acid groups so that there is no free acid at the time of dispersion.

In the aqueous dispersion the isocyanate terminated prepolymer is chain extended and terminated by reaction with primary or secondary amine functional compounds. The final dispersed polymer is therefore a poly(urethane/urea). The chain extenders used are preferably water soluble compounds as these increase the dispersibility of the polymer end product in water. Organic diamines are preferably used because they generally provide the maximum increase in molecular weight without causing gelling of the poly (urethane/urea) dispersion. Useful chain extenders include aliphatic, cycloaliphatic, and aromatic diamines. Examples of suitable diamines are ethylenediamine (EDA), propylenediamine, 1,4-butylenediamine, piperazine, 1,4-cyclohexyldimethyldiamine, hexamethylenediamine (HDI), N-methylpropylenediamine, diaminophenylsulfone, diaminodiphenylether, diaminodiphenyldimethylmethane, 2,4-diamino-6-phenyltriazine, isophoronediamine, dimer fatty acid diamine, N-isodecycloxy propyl-1,3-diaminopropane and imidazolidinone functional diamines. Polyamine compounds having terminal primary amine groups as well as internal secondary amine groups, such as diethylene triamine (DETA), and triethylene tetraamine may also be employed. Some crosslinking in the dispersed poly (urethane/urea) polymer may be provided through the secondary amine of such compounds, but such crosslinking can be kept low by appropriate stoichiometric adjustments.

Examples of useful chain terminators include aminoalcohols, like ethanolamine, propanolamine, butanolamine, N-methylethanolamine, N-methylisopropanolamine, taurine and isethionic acid.

The compositions of the invention may be crosslinked by adding a crosslinker to the dispersion at, or shortly before, the time it is applied to a substrate and dried. Conventional polyisocyanate crosslinkers may not be suitable for this purpose since the polymer preferably has little or no terminal amine groups. However, crosslinking can be accomplished through the carboxylate groups introduced into the sulfonated polyurethane polymer via the hydroxy carboxylic acid component of the polyol component. The carboxylate groups are reacted with carboxylic acid reactive crosslinkers which are active at room temperature, such as polyfunctional aziridine compounds, zinc ammonium carbonate, zirconium carbonate or polyfunctional carbodiimide compounds. Typically crosslinkers are added at a level of 1–10% by weight.

The compositions may be used in automobiles, bonding polypropylene foam to polyvinyl chloride at activation temperature of about 90°–110° C.; in aerospace, bonding of DuPont Tedlar® PVF to phenolic composite at activation temperatures in the range of from room temperature to 100° C.; in shoemaking, bonding leather to SBR (activation temperature 60°–90° C.), and bonding highly plasticized PVC to itself or other substrates (activation temperature 60°–90° C.); in woodworking, bonding PVC to medium density fiberboard (activation temperature 60°–90° C.); in bookbinding, bonding paper to paper using activation temperatures from room temperature to 95° C.; in house siding for bonding Tedlar® to PVC, wood, wood composite, recycled wood and/or paper products; and in laminating of films of polyethylene terephthalate to films of polypropylene, polyethylene or aluminum or other metal foils (activation temperatures of 50°–70° C.).

The formulations of the invention have good compatibility with other water based polymer dispersions even those having low pH (pH 4–7). This compatibility makes the formulations of the invention useful in blends with acrylic, epoxy and vinyl acetate or other vinyl polymer dispersions, as well as other polyurethane polymer dispersions. Blends with water based acrylic polymers can be used for shoe and fiberglass sizing applications. Blends with vinyl acetate or other vinyl polymer dispersions have use in automotive, woodworking, and bookbinding applications.

The invention is further illustrated, by the following non-limiting examples in which all parts and percentages are by weight unless otherwise specified.

EXAMPLES

Heat resistance

Heat resistance reported for the polyurethane dispersion adhesives described in the following examples were obtained by drawing down the dispersion with or without a crosslinker on a 10 mil clear PVC film (polyvinyl chloride film from Laird Plastics) with a #28 Mylar rod to prime a 2.5×2.5 cm (1×1 inch) area of 2.5 cm wide strips of the PVC films. After the adhesive is dry to touch the primed PVC film is cut into 2.5×5 cm (1×2 inch) strips. The primed strip is heat sealed to another uncoated 2.5×5 cm PVC strip using a Sentinal Heat Sealer at 345 kPa (50 psi) nip pressure with a 30 second dwell time. The sealing temperatures (activation temperature) selected were as listed in Table 2. The bonds were allowed to age 7 days and then the heat resistance temperature was measured.

A 100 g weight was attached to each PVC bond in a T-peel configuration and then placed in the Tenney oven. The T-peels had a 1 square inch bond area. The T-peels were subjected to a 25° C. increase in temperature each hour until 127° C. (260° F.). The temperatures were recorded by the Tenney sensing unit upon bond failure.

Abbreviations

The following abbreviations are used in the Examples:

| | |
|---|---|
| Rucoflex XS-5483-55 | a sulfonated polyester polyol based on 5-sulfoisophthalic acid monosodium salt, adipic acid and 1,6-hexanediol, OH number 49.0 |
| DMPA | dimethylolpropionic acid |
| 1,4-BD | 1,4-butanediol |
| IPDI | isophorone diisocyanate |
| HDI | hexamethylenediisocyanate |
| TMXDI | Tetramethylxylyenediisocyanate |
| EDA | ethylenediamine |
| TEA | triethylamine |
| MEK | methyl ethyl ketone |

Example 1

Rucoflex XS-5483-55, 213.8 g, 10.05 g of DMPA and 11.25 g of 1,4-BD were reacted with 31.08 g of IPDI and 47.04 g of HDI in the presence of 18.1 g of acetone at 70° C. for 3 hours to prepare a prepolymer. TEA, 6.0 g, was then added to the prepolymer solution to neutralize the carboxylic acid groups in the prepolymer. Then 554.3 g of water was added to disperse the neutralized prepolymer, immediately followed by 5.4 g of EDA in 50.0 of water to form the aqueous polyurethane dispersion. A finely divided dispersion having a solids content of 34.9% a pH of 7.0 and an acetone content of 1.9% was obtained.

A film was cast from this aqueous polyurethane dispersion. Portions of the cast film were immersed, respectively in water at room temperature for 24 hours and in MEK for 7 days. In both cases the film remained very strong after immersion, indicating very good water and solvent resistance.

The heat resistance results are shown in Table 2.

Example 2

Rucoflex XS-5483, 213.8 g, 10.05 g of DMPA and 9.0 g of 1,4-BD were reacted with 28.53 g of IPDI and 42.84 g of HDI in the presence of 18.1 g of acetone at 70° C. for 3 hours to prepare a prepolymer. TEA, 8.0 g, was then added to the prepolymer solution to neutralize the part of the carboxylic acid groups in the prepolymer. Water, 520.9 g, was added to disperse the neutralized prepolymer and then 4.95 of EDA and 50.0 of water were immediately added to form the aqueous polyurethane dispersion. A finely divided dispersion having a solids content of 34.9%, a pH of 8.6 and an acetone content of 2.0% was obtained.

Portions of a film made from this dispersion were immersed in water for 24 hours and in MEK for 7 days, respectively, after which they remained very strong.

The heat resistance is shown in Table 2.

Example 3

The preparation method for Example 3 was same as the method in the Example 1, except the neutralized prepolymer was dispersed in water in a open plastic container with stirring. A finely divided dispersion having a solids content of 35.0%, a pH of 7.2 and an acetone content of 1.0% was obtained.

Portions of a film made from the dispersion were immersed, respectively, in water for 24 hours, or in MEK for 7 days, after which they were still very strong.

The heat resistance is shown in Table 2.

Example 4 (Comparative Example)

In this example, a film was cast from Dispercoll KA-8464, an aqueous polyurethane dispersion product of Bayer Corporation, based on sulfonated aliphatic diamine, HDI and IPDI made by a 40–80% acetone process based on U.S. Pat. No. 4,870,129. After immersion in water for 24 hours at room temperature, a film made from this dispersion became very weak and totally lost resistance to stress. Another film made from this dispersion was immersed in MEK for 7 days, and totally dissolved.

The heat resistance is shown in Table 2.

TABLE 2

| Heat resistance temperature (°F.) (PVC/PVC) | | | | |
|---|---|---|---|---|
| Activation temp (°F.) | 125 | 150 | 175 | 200 |
| Example 1 | >260 | >260 | >260 | >260 |
| Example 2 | 242 | 242 | 247 | 242 |
| Example 3 | >260 | >260 | >260 | >260 |
| Example 4 | 199 | 220 | 221 | 223 |

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

Example 5

Rucoflex XS-5483, 45.39 kg, 2.13 kg of DMPA and 2.39 kg of 1,4-BD were reacted with 6.60 kg of IPDI and 9.99 kg of HDI in the presence of 4.24 kg of acetone at 70° C. for 2.5 hours to prepare a prepolymer. TEA, 1.27 kg, was added to the prepolymer to neutralize the carboxylic acid groups in the prepolymer. The neutralizer was mixed for 15 minutes.

The prepolymer was dispersed in water with an in-line, continuous mixing process. The mixer used to obtain the dispersion was a T.K. Homomic Line Flow 100S manufactured by Tokushu Kika Kogyo Co., Ltd. Prepolymer was fed to the mixer through a gear pump at a rate of 3.60 kg.min and a temperature of 80° C. Water was fed to the mixer at a rate of 6.40 kg/min and a temperature of 60° C. The average residence time in the mixer was maintained at 61 seconds with an agitator speed of 3600 RPMs.

The dispersion was transferred to a finishing vessel equipped with a turbine agitator and run at a circulation rate of between 5 and 10 min$^{-1}$. A 9.78% solution of EDA in water was added to the finishing vessel. The finished dispersion was mixed for 30 minutes at a temperature of 60° C. after completing addition of the dispersion and diamine solutions.

A finely divided aqueous polyurethane dispersion having a solids content of 31.38%, a pH of 7.9, an average particle size of 189 nm, and a viscosity of 36 cps was obtained.

What is claimed is:

1. A method for forming a stable aqueous dispersion of an anionic poly(urethane/urea) polymer, the dispersion comprising 0.1–5% by weight of the dispersion of volatile solvents, the method comprising reacting, at a temperature of from room temperature to 100° C. and in the presence of a water soluble volatile organic solvent at a level corresponding to no more than 5% by weight of the final dispersion, a polyisocyanate component comprising a diisocyanate, with a polyol component to produce an isocyanate terminated polyurethane prepolymer, the polyol component providing both anionic carboxylate groups and anionic sulfonate groups to the dispersed poly(urethane/urea) polymer and the polyol component comprising at least one sulfonated polyester polyol;

dispersing the isocyanate terminated prepolymer in water; and reacting said dispersed isocyanate terminated prepolymer with at least one amine functional chain extender or chain terminator compound to thereby form said poly (urethane/urea) polymer;

said anionic carboxylate and anionic sulfonate groups being formed by neutralization of carboxylic acid and sulfonic acid groups, respectively, with an alkali hydroxide or a tertiary amine prior to, or simultaneously with, said reaction of said prepolymer and said amine functional chain extender or terminator;

wherein said method is performed without a solvent distillation step.

2. A method as in claim 1 wherein said solvent is selected from the group consisting of acetone, 1-methyl-2-pyrrolidone, dipropylene glycol methyl ether acetate, and methyl ethyl ketone.

3. A method as in claim 1 wherein said solvent is employed at a level corresponding to between about 0.1 and about 3% by weight of the final dispersion.

4. A method as in claim 1 wherein said water is added in an amount to provide the dispersion with a solids content of between about 20 and 50% by weight.

5. A method as in claim 1 wherein the polyol component comprises at least one sulfonated polyester, the sulfonated polyester characterized by number average molecular weights in the range of about 500 to 10,000 and melting temperatures between about 10° C. and 100° C.; and at least one hydroxy carboxylic acid of the formula:

wherein R represents a straight or branched, hydrocarbon radical containing 1 to 12 carbon atoms, and x and y represent values from 1 to 3, provided, however, that when the value of x is 1, an equivalent amount of trifunctional isocyanate is employed in the polyisocyanate component and when x is 3, an equivalent amount of monofunctional isocyanate is employed whereby the resulting polyurethane prepolymer remains substantially non-crosslinked.

6. A method as in claim 5 wherein the hydroxy carboxylic acid is an α,α-dimethylol alkanoic acid represented by the formula:

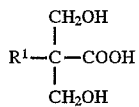

where $R^1$ denotes hydrogen or an alkyl group with up to about 9 carbon atoms.

7. A method as in claim 6 wherein the hydroxy carboxylic acid is selected from the group consisting of 2,2-dimethylolacetic acid, 2,2-dimethylolpropionic acid (DMPA), 2,2-dimethylolbutyric acid and 2,2-dimethylolpentanic acid.

8. A method as in claim 7 wherein the hydroxy carboxylic acid is 2,2-dimethylolpropionic acid.

9. A method as in claim 6 wherein said polyol component further comprises a non-sulfonated polyester which is free of ethyleneoxyethylene groups.

10. A method as in claim 6 wherein said polyol component further comprises a non-acidic diol having a molecular weight between about 60 and about 400.

11. A method as in claim 6, wherein the hydroxy carboxylic acid is 2,2-dimethylolpropionic acid, the solvent is acetone and the water is added in an amount to provide a solids content of about 30 to about 40% by weight of the final dispersion.

12. A method as in claim 5 wherein said sulfonated polyester polyol is a polyester of a sulfonated diacid or sulfonated diol, a non-sulfonated diacid and a non-sulfonated diol.

13. A method as in claim 12 wherein said non-sulfonated diacid is selected from the group consisting of adipic, azelaic, succinic, suberic and phthalic acids, and mixtures thereof.

14. A method as in claim 12 wherein non-sulfonated diol is selected from the group consisting of ethylene glycol, butanediol, butenediol, propanediol, neopentylglycol, hexanediol, 1,4-cyclohexane dimethanol, 1,2-propylene glycol and 2-methyl-1,3-propanediol, and mixtures thereof.

15. A method as in claim 12 wherein the sulfonated diacid or sulfonated diol is selected from the group consisting of sulfoisophthalic acid, sulfosuccinic acid, 1,4-dihydroxybutane sulfonic acid and succinaldehyde disodium bisulfite.

16. A method as in claim 5 wherein said sulfonated polyester polyol has a number average molecular weight in the range of about 1,000 to 4,000.

17. A method as in claim 16 wherein the sulfonated polyester polyol has a melting temperature in the range of 40° C. to 60° C.

18. A method as in claim 5 wherein the sulfonated polyester polyol is a polyester of 5-sulfoisophthalic acid monosodium salt, 1,6-hexanediol and adipic acid.

19. A method as in claim 1 wherein the polyisocyanate component comprises hexamethylene diisocyanate (HDI).

20. A method as in claim 19 wherein the polyisocyanate is a mixture of HDI and a second diisocyanate.

21. A method as in claim 20 wherein the second diisocyanate is a member of the group consisting of isophorone diisocyanate (IPDI), cyclopentylenediisocyanate, cyclohexylenediisocyanate, methylcyclohexylenediisocyanate, dicyclohexylmethanediisocyanate, dicyclohexylmethanediisocyanate (H12MDI), tetramethylxylenediisocyanate (TMXDI), phenylenediisocyanate, tolylenediisocyanate (TDI), xylylenediisocyanate, biphenylenediisocyanate, naphthylenediisocyanate and diphenylmethanediisocyanate (MDI).

22. A method as in claim 1 wherein said amine functional chain extender is a member of the group consisting of ethylenediamine (EDA), propylenediamine, 1,4-butylenediamine, piperazine, 1,4-cyclohexyldimethyldiamine, hexamethylenediamine (HDA), N-methylpropylenediamine, diaminophenylsulfone, diaminodiphenylether, diaminodiphenyldimethylmethane, 2,4-diamino-6-phenyltriazine, isophoronediamine, dimer fatty acid diamine, N-isodecycloxy propyl-1,3-diaminopropane, imidazolidinone functional diamines, diethylene triamine (DETA), triethylene tetraamine, and mixtures thereof.

23. A method as in claim 1 wherein said isocyanate terminated prepolymer is reacted with a mixture of at least one amine functional chain extender compound and at least one chain terminator compound.

24. A method as in claim 23 wherein the chain extender is present in said mixture of chain extender and chain terminator in an amount of at least 50% by weight of said mixture of chain extender and chain terminator.

25. A method as in claim 24 wherein said chain extender is a member of the group consisting of ethylene diamine, diethylene triamine, and mixtures thereof and said chain terminator is ethanolamine.

26. A method as in claim 1 wherein said prepolymer forming reaction step is performed at a temperature of between ambient room temperature and 100° C.

27. A method as in claim 1 wherein said polyol component is free of compounds comprising ethyleneoxyethylene groups.

28. A method as in claim 1 wherein said solvent is employed at a level corresponding to 0.5%–2% by weight of the final dispersion.

* * * * *